(12) United States Patent
Sheldon (10) Patent No.: US 7,356,854 B2
(45) Date of Patent: Apr. 15, 2008

(54) GOGGLES WITH FLEXIBLE SIDE MOUNTING TABS

(76) Inventor: Neville Sheldon, 315 Putney, St. Lambert, Quebec (CA) J4P 2B5

(*) Notice: Subject to any disclaimer, the term of this patent is extended or adjusted under 35 U.S.C. 154(b) by 164 days.

(21) Appl. No.: 11/299,966

(22) Filed: Dec. 13, 2005

(65) Prior Publication Data

US 2007/0130675 A1    Jun. 14, 2007

(51) Int. Cl.
*A61F 9/02*    (2006.01)
(52) U.S. Cl. .......................................................... 2/448
(58) Field of Classification Search .................... 2/448, 2/430, 449, 450, 451, 439, 440, 442, 9, 12, 2/15; 351/104, 111
See application file for complete search history.

(56) References Cited

U.S. PATENT DOCUMENTS

| | | | |
|---|---|---|---|
| 5,642,178 A * | 6/1997 | Leonardi et al. ............ | 351/111 |
| 5,829,064 A * | 11/1998 | Huang ............................ | 2/428 |
| 6,715,157 B2 * | 4/2004 | Mage ............................. | 2/439 |
| 6,732,383 B2 | 5/2004 | Cleary et al. | |
| 6,928,663 B1 | 8/2005 | Tappeiner | |
| 6,929,364 B1 | 8/2005 | Jannard | |
| 2003/0221246 A1 * | 12/2003 | Schary et al. .................. | 2/453 |

* cited by examiner

*Primary Examiner*—Katherine Moran
(74) *Attorney, Agent, or Firm*—Ogilvy Renault LLP (57) ABSTRACT

Eyewear such as goggles having a frame made of a first material and a pair of side mounting tabs secured to the frame at the respective opposite side ends thereof for attachment with a head support such as a head strap. The side mounting tabs are made of a second material which is resilient in order to provide a flexibility of the tabs to allow the tabs to flip over such that the user can comfortably wear the goggles with or without a helmet.

12 Claims, 6 Drawing Sheets

GOGGLES WITH FLEXIBLE SIDE MOUNTING TABS

TECHNICAL FIELD

The present invention relates to eyewear, and more particularly to goggles having flexible side mounting tabs.

BACKGROUND OF THE INVENTION

Goggles are widely used in a variety of applications such as by skiers, snow-boarders and other outdoors enthusiasts, as well as people working in hazardous conditions or with hazardous substances, in order to protect their eyes from sun, wind, snow, debris and contaminants. In some cases, such as in skiing and snow-boarding, helmets are also used to protect the skiers' and snow-boarders' heads from potential impacts. Most conventional goggles are configured to be comfortably and effectively worn without a helmet, but do not fit well over helmets. A helmet interferes with the goggles straps where the straps meet the goggles body, which causes the goggles frame to become deformed, thereby forming a gap between the goggles and the user's face where light, air or debris may enter. For example, many ski and snow-board goggles have a curved frame that approximates the shape of the user's face. The head strap on these goggles is typically attached at the outermost sides of the goggles frame near the user's temples. Such an arrangement permits the head strap to pull the goggles frame back and towards the user's face. Nevertheless, when the goggles are used with a helmet, the head strap extends around the outside of the helmet and is pushed out and away from the user's temples by the portion of the helmet at the sides of the user's face. This causes a lateral force pulling on the sides of the goggles frames to disengage the goggles frame from the user's face.

To address this problem, some types of conventional goggles are formed with outward extensions to offset the strap from the goggles frame in order to reduce interference between the helmet and the head straps. However, those types of goggles are less attractive and less comfortable when worn without a helmet.

Goggles having hinge mechanisms have been developed for use either with or without a helmet. The hinge mechanisms are pivotable about a pivoting joint on the goggles frames in order to provide different positions of attachment of the head strap to the goggles frame.

Nevertheless, there are also shortcomings in goggles with hinge mechanisms. Accordingly, alternative and improved goggle configurations are desirable.

SUMMARY OF THE INVENTION

One object of the present invention is to provide eyewear having flexible side mounting tabs.

In one aspect of the present invention there is eyewear which comprises at least one lens and one frame made of a first material, having opposite side ends thereof. The frame secures the at least one lens thereto. There are means contoured for surrounding and shielding the eyes of a user. A head support is provided for holding the eyewear on a user's head in a manner such that said means are forced to abut an area around the eyes of the user. A pair of side mounting tabs having opposite first and second ends thereof are secured at the first end thereof to the respective side ends of the frame. The head support is attached to the respective side mounting tabs at the second end thereof. The side mounting tabs are made of a resilient second material to provide a flexibility of the tabs.

In accordance with another aspect of the, present invention there is a pair of goggles which comprise a pair of lenses and a frame made of a first material, having opposite side ends thereof. The frame secures the pair of lenses thereto. One or more shielding members are attached to the frame and contoured for surrounding and shielding the eyes of a user. A flexible and resilient strap is provided for holding the goggles on the head of the user. A pair of side mounting tabs are integrally secured to the frame at the respective opposite side ends thereof for attachment of the strap. The side mounting tabs are made of a second material which is flexible and resilient.

In accordance with a further aspect of the present invention, there is provided eyewear comprising at least one lens and a frame having opposite side ends thereof. The frame secures the at least one lens thereto. Means are provided which are contoured for surrounding and shielding the eye of a user and a head support is provided for holding the eyewear on a user's head in a manner such that said means are forced to abut an area around the eyes of the user. A pair of side mounting tabs are secured to the respective side ends of the frame, the head support being attached to the respective side mounting tabs. The side mounting tabs are integrally made together with the frame from a material having a resilient property, to form flexible extensions of the respective side ends thereof, in order to allow displacement of an attachment position of the head support to the side mounting tabs, with respect to the frame.

Other features of the present invention will be better understood with reference to the embodiments described hereinafter.

BRIEF DESCRIPTION OF THE DRAWINGS

Reference will now be made to the accompanying drawings showing by way of illustration the preferred embodiments, in which.

DETAILED DESCRIPTION OF THE PREFERRED EMBODIMENT

Figure 1:
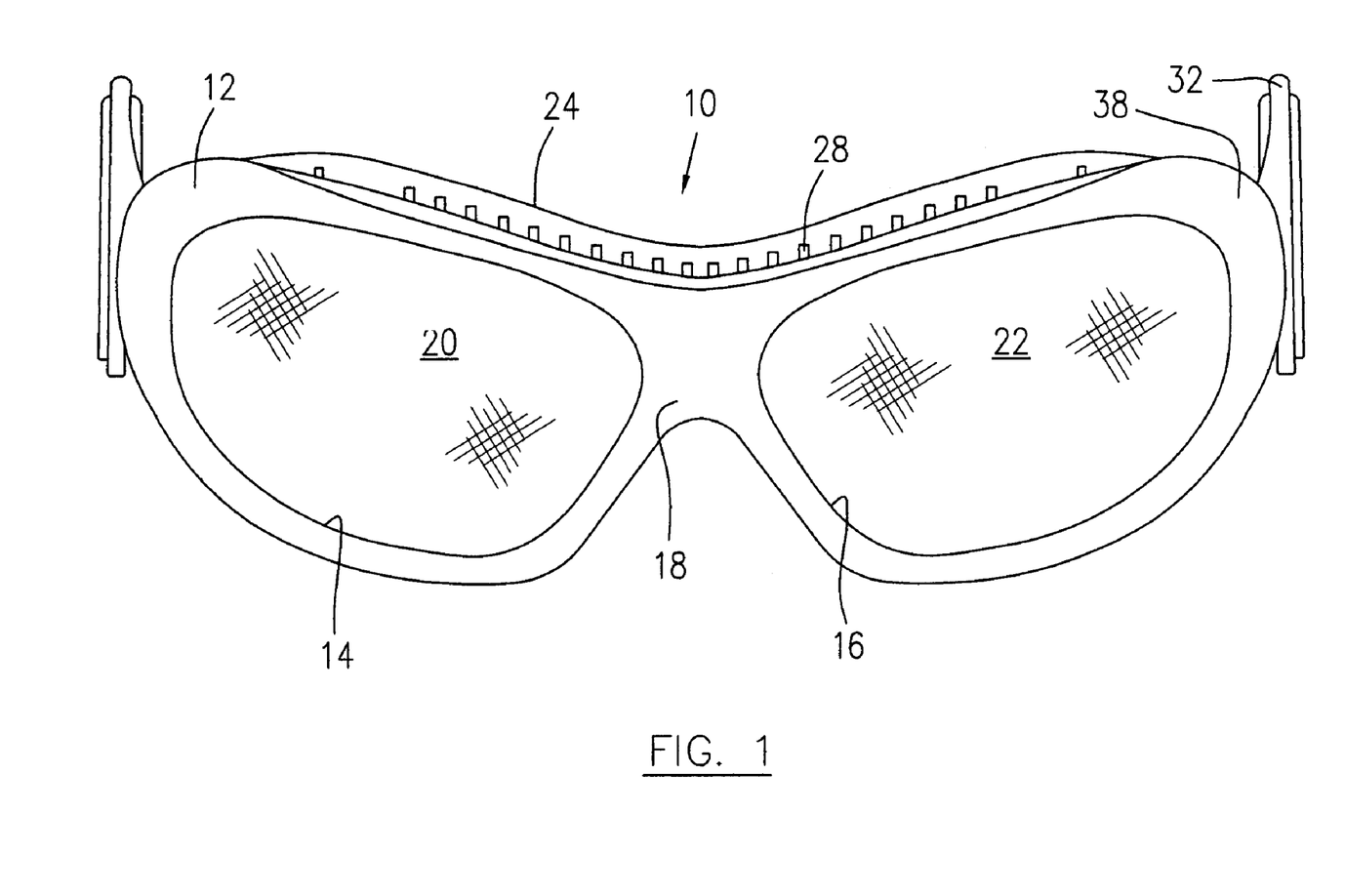
FIG. 1 is a front elevational view of a pair of goggles according to one embodiment of the present invention, with a head strap removed.
Figure 2:
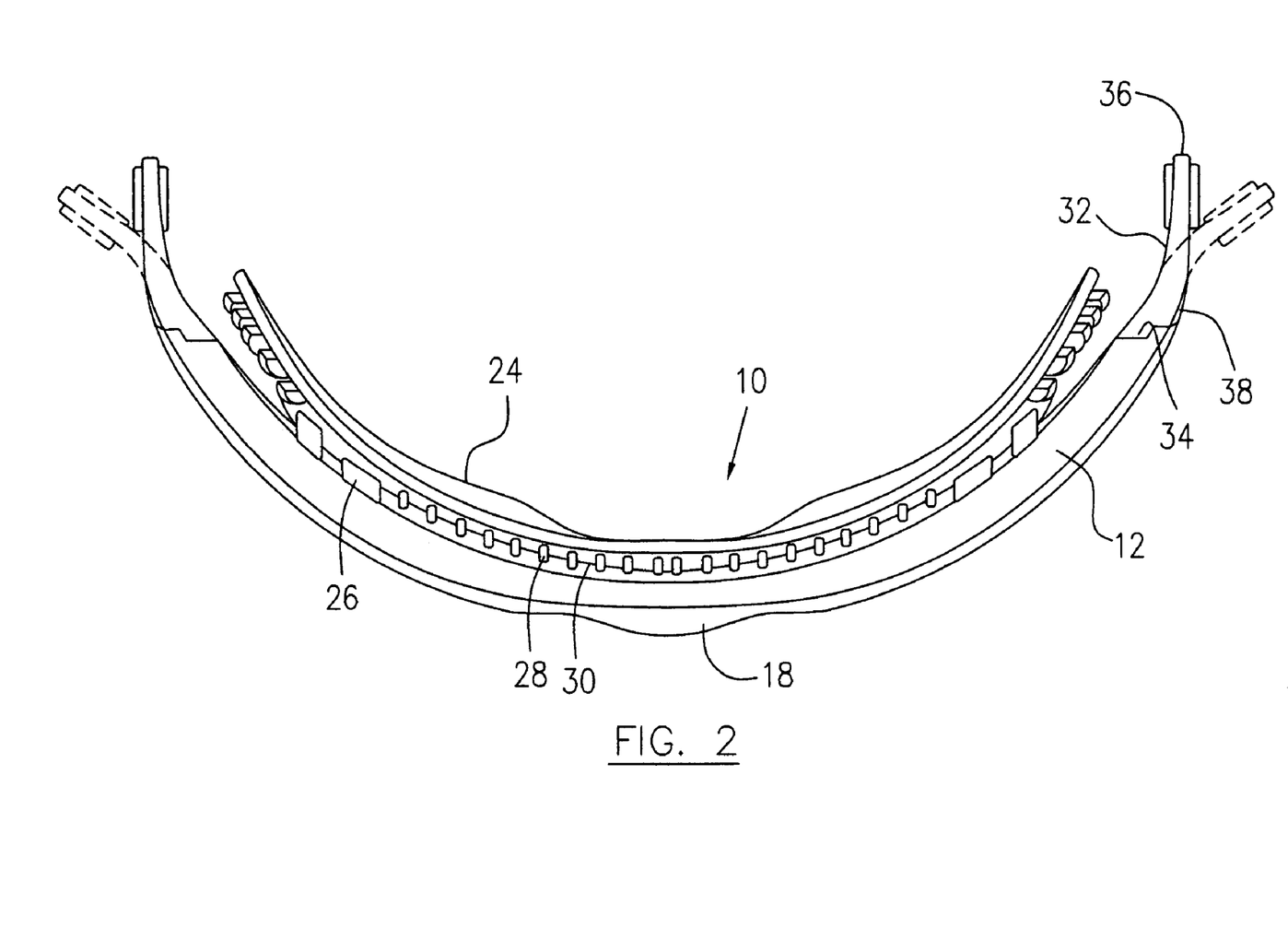
FIG. 2 is a top plane view of the goggles of FIG. 1, showing the flexible side mounting tabs adapted to be deviated in different positions.
Figure 3:
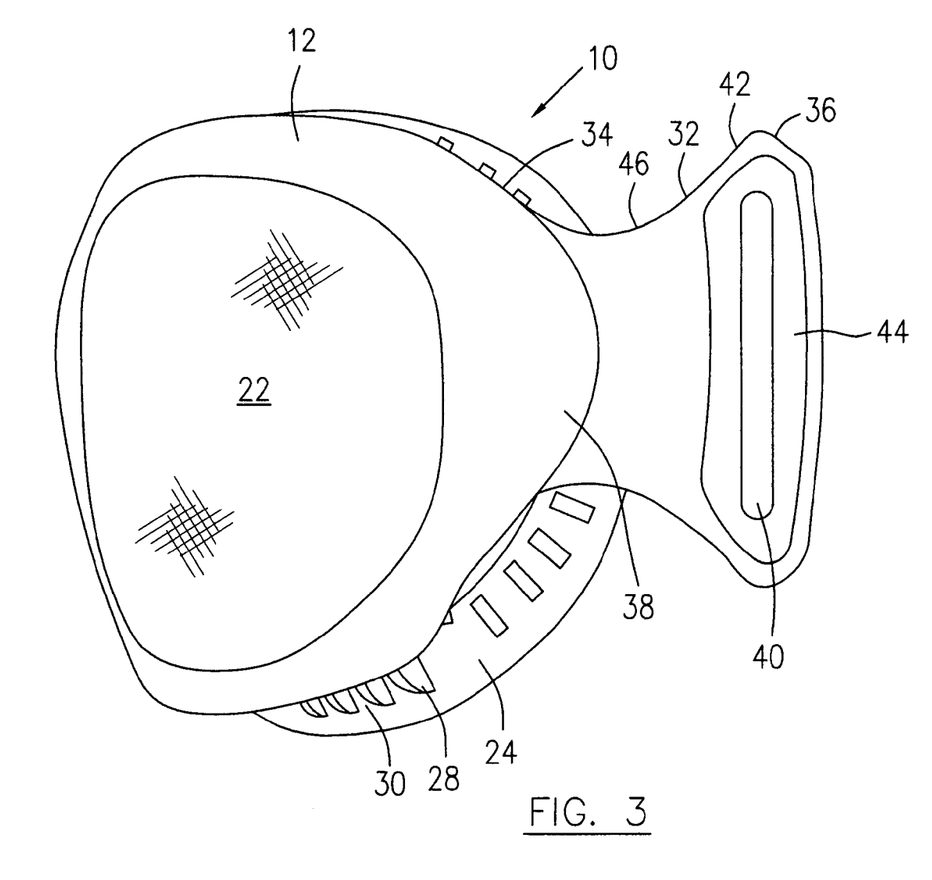
FIG. 3 is a side elevational view of the goggles of FIG. 1, showing the details of the side mounting tab thereof.

In FIGS. 1-3, eyewear of the present invention according one embodiment thereof is shown as a pair of goggles, generally indicated by reference numeral 10 which includes a frame 12. The frame 12 defines openings 14, 16 therein which are separated by a nose portion 18 positioned therebetween. A pair of lenses 20, 22 are secured to the frame 12 within the respective openings 14 and 16. The attachment of the respective lenses 20, 22 to the frames 12 can be in various known manners such as removable or permanent attachment, with or without retaining rims, etc., which are not part of the present invention and will not be discussed in detail. The frame 12 is made of a substantially rigid material, such as rigid plastics, for providing and maintaining a desirable shape and style of the goggles.

A shielding member 24 is attached to the frame 12 at an inner surface thereof and is contoured for surrounding and shielding the eyes of a user.

In particular, the shielding member 24 is made of a relatively resilient material with respect to that of the frame 12, for example, a rubber strip formed in a continuous loop substantially similar to the outer periphery of the frame 12. Thus, the shielding member 24 surrounds both eyes and comfortably abuts the face of the user when the goggles 10 are worn on the head of the user. The upper portion (not indicated) and the lower portion (not shown) of the rubber strip may or may not be connected together at the middle section behind the nose section 18 of the frame 12. The shielding member 24 is secured to the inner surface of the frame 12 by means of a number of spacers 26 and is thus spaced apart from the inner surface of the frame 12 in order to provide a gap between the inner surface and the shielding member 24. The shielding member 24 further includes a plurality of ribs 28 distributed in a spaced relationship one to another along the entire periphery of the shielding member 24 such that the gap between the inner surface of the frame 12 and the shielding member 24 is substantially divided into a plurality of air passages 30. Air flow can be thus directed through the air passages 30 and into the space between the goggles 10 and the eyes of the user when the goggles 10 are worn on the head of the user.

Goggles 10 further includes a pair of side mounting tabs 32 made for example of a flexible and resilient plastic material or rubber. Each side mounting tab 32 has opposite ends. An inner end 34 is attached, preferably integrally secured, to one of opposite side ends 38 of the frame 12. An outer end 36 is adapted for attachment to a head support (not shown) such as a head strap which holds the goggles 10 on the user's head such that the shielding member 24 is forced to abut an area around the eyes of the user. The head support is well known in the art and will not be described in detail herein.

The flexible and resilient side mounting tabs 32 when pulled by the head support or the head strap from different angles, will be deviated over a range of angles (as shown with broken lines in FIG. 2), in order to offset the position change of the connection portion of the head strap caused by whether or not the helmet is worn by the user, thereby functioning similarly to the conventional hinges provided with goggles. Nevertheless, in contrast to the conventional hinges on goggles, the flexible side mounting tabs 32 provide a more aesthetic styling in the integration thereof to the frame 12. Furthermore, the flexible and resilient side mounting tabs 32 substantially eliminate possible malfunctions of the conventional hinges on goggles caused by, for example, being clogged by snow or debris.

The inner end 34 of the side mounting tab 32 can be integrally secured to the side end 38 of the frame 12, preferably at the inner side thereof, for example, by adhesive. If the side mounting tab 32 is to be made of a moldable material such as a resilient plastic material, it can be directly molded onto the side end 38 of the frame 12. The interface between the inner end 34 of the side mounting tab 32 and the side end 38 of the frame 12 can be configured in various mating configurations in order to increase the connection area therebetween, thereby strengthening the attachment.

The head support or head strap is attached to the outer end 36 of the side mounting tab 32 in any know manner. In this embodiment an opening 40 is defined in a section 42 which is located at the outer end 36 of the side mounting tab 32, for attachment of the head support or head strap. It is preferable to have the section 42 enlarged in one dimension in order to accommodate a relatively wide head strap to be attached thereto.

It is further preferable that the section 42 is reinforced by a relatively rigid attachment element 44 which defines the opening 40, for attachment of the head support or head strap. The attachment element 44 provides protection for the section 42 from potential damage caused by a pulling force of the head support or head strap acting on the opening-weakened area. Furthermore, the relatively rigid attachment element 44 reinforces the section 42 such that the side mounting tab 32 is less flexible and less resilient at the section 42 than at an intermediate section 46 thereof located between the section 42 and the section proximate to the inner end 34 of the side mounting tab 32 which is secured to the frame 12. This feature ensures that the bend of the side mounting tab 32 is more likely to occur at the intermediate section 46 when the side mounting tab 32 is needed to flip over to offset the position of the head support or head strap which is deviated by a helmet worn on the user's head. In this embodiment, the material used for the attachment element 44 is the same as that of the substantially rigid frame 12. The configuration of the attachment element 44 will be better understood when another embodiment of the present invention is described.

Figure 4:
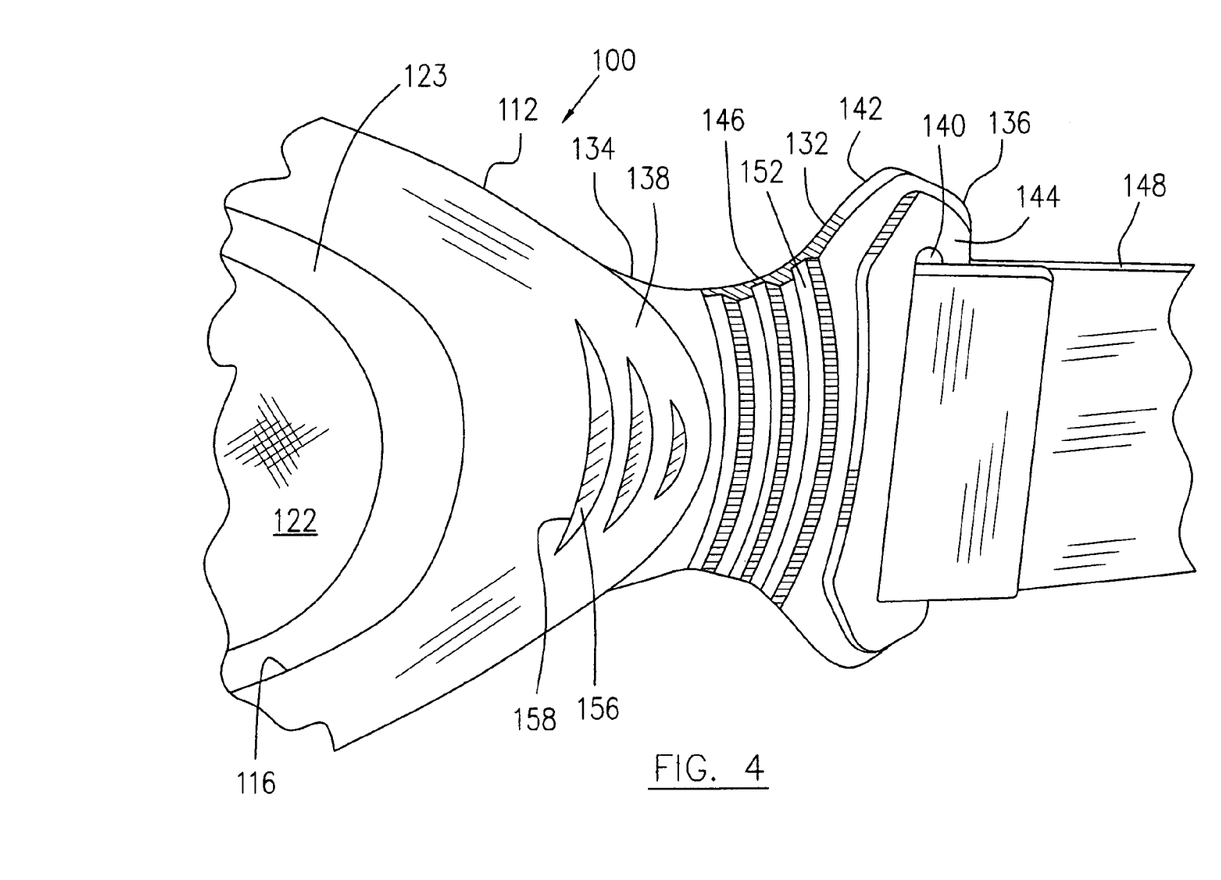
FIG. 4 is a partial perspective view of a pair of goggles according to another embodiment of the present invention, showing a side mounting tab in detail.
Figure 5:
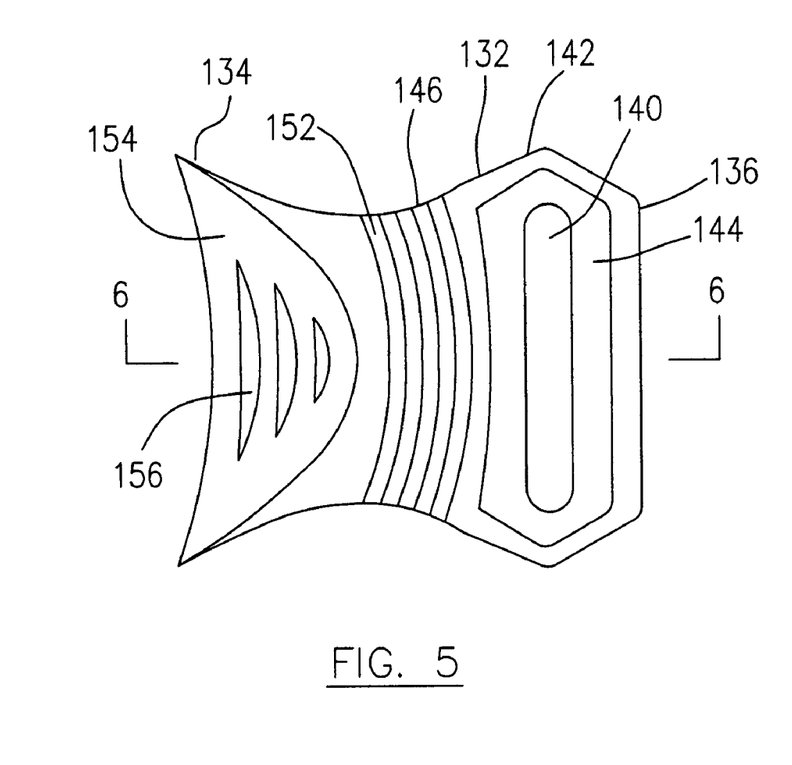
FIG. 5 is a side elevational view of the flexible side mounting tab for use in the goggles of FIG. 4.
Figure 6:
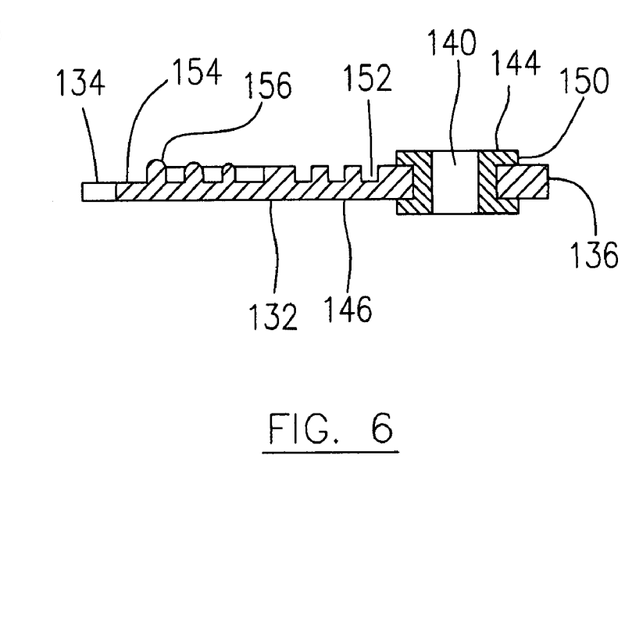
FIG. 6 is a cross-sectional view of the flexible side mounting tab, taken along line 6-6 in FIG. 5.

In FIGS. 4-6 the eyewear of the present invention illustrated as a pair of goggles 100 according to another embodiment of the present invention, is similar to the goggles 10 of FIG. 1. Generally, goggles 100 includes a frame 112 made of a material, preferably a substantially rigid plastic material, defining a pair of openings (only one opening 116 is shown) and having a nose section (not shown) positioned therebetween. A pair of lenses (only one lens 122 is shown) are encircled by respective rims (only one rim 123 is shown) which are in turn attached to the frame 112 within the respective openings. Shielding means (not shown) which may be similar to the shielding member 24 of FIG. 1, are attached to the inner surface of the frame 122 and contoured for surrounding and shielding the eyes of a user. A pair of side mounting tabs 132 (only one shown) are attached to respective opposite side ends 138 (only one shown) of the frame 112 for attachment thereto of a head support such as a flexible and resilient head strap 148.

Similar to side mounting tabs 32 shown in FIGS. 1-3, the side mounting tab 132 has opposite ends: an inner end 134 which is integrally or permanently attached to the side end 138 of the frame 112 and an outer end 136 with a reinforced section 142 for attachment of the head strap 148 thereto. In particular, the side mounting tab 132 defines an opening (not indicated) for receiving an elongate attachment element 144 therein. The elongate attachment element 144 includes a flange 150 at each side thereof to prevent the attachment element 144 from being removed from the side mounting tab 132. An elongate opening 140 is defined through the attachment element 144 in order to permit the head strap 148 to extend therethrough such that the head strap 148 forms an end loop connected with the side mounting tab 132.

The side mounting tab 132 is made of, for example, flexible and resilient rubber or plastic material, and the attachment element 144 is made of substantially rigid material, such as metal or plastic. A plurality of grooves 152 are preferably defined on the outer surface of the side mounting tab 132 at an intermediate section 146 thereof which is positioned between the reinforced section 142 at the outer end 136 of the side mounting tab 132 and the section at the inner end 134 of the side mounting tab 132, which is to be attached to the side end 138 of the frame 112. The grooves 152 extend between the top and the bottom of the tab 132 to increase the flexibility thereof, particularly in the intermediate section 146.

The section at the inner end 134 of the side mounting tab 132 preferably defines a recess 154 contoured for receiving the side end 138 of the frame 112 when the inner end 134 of the side mounting tab 132 is attached to the inner surface of the frame 112 at the side end 138 thereof. In order to strengthen the permanent attachment of the side mounting tab 132 to the frame 112, the side mounting tab 132 is preferably provided with one or more inserts 156 projecting from the bottom of the recess 154. One or more complementary openings 158 are defined in the frame 112 at the side end 138 thereof for snuggly receiving the inserts 156 such that the inserts 156 project into the frame 112 towards the external surface of the frame 112 when the side mounting tab 132 is attached to the frame 112. Thus, the inserts 156 will contribute to the load bearing when the goggles 100 are worn on the head of a user and the head strap 148 is applying a pulling force on the side mounting tab 132. This will significantly increase the durability of the attachment of the side mounting tab 132 to the frame 112 regardless of the nature of the attachment, such as being glued or molded thereto.

Figure 7:
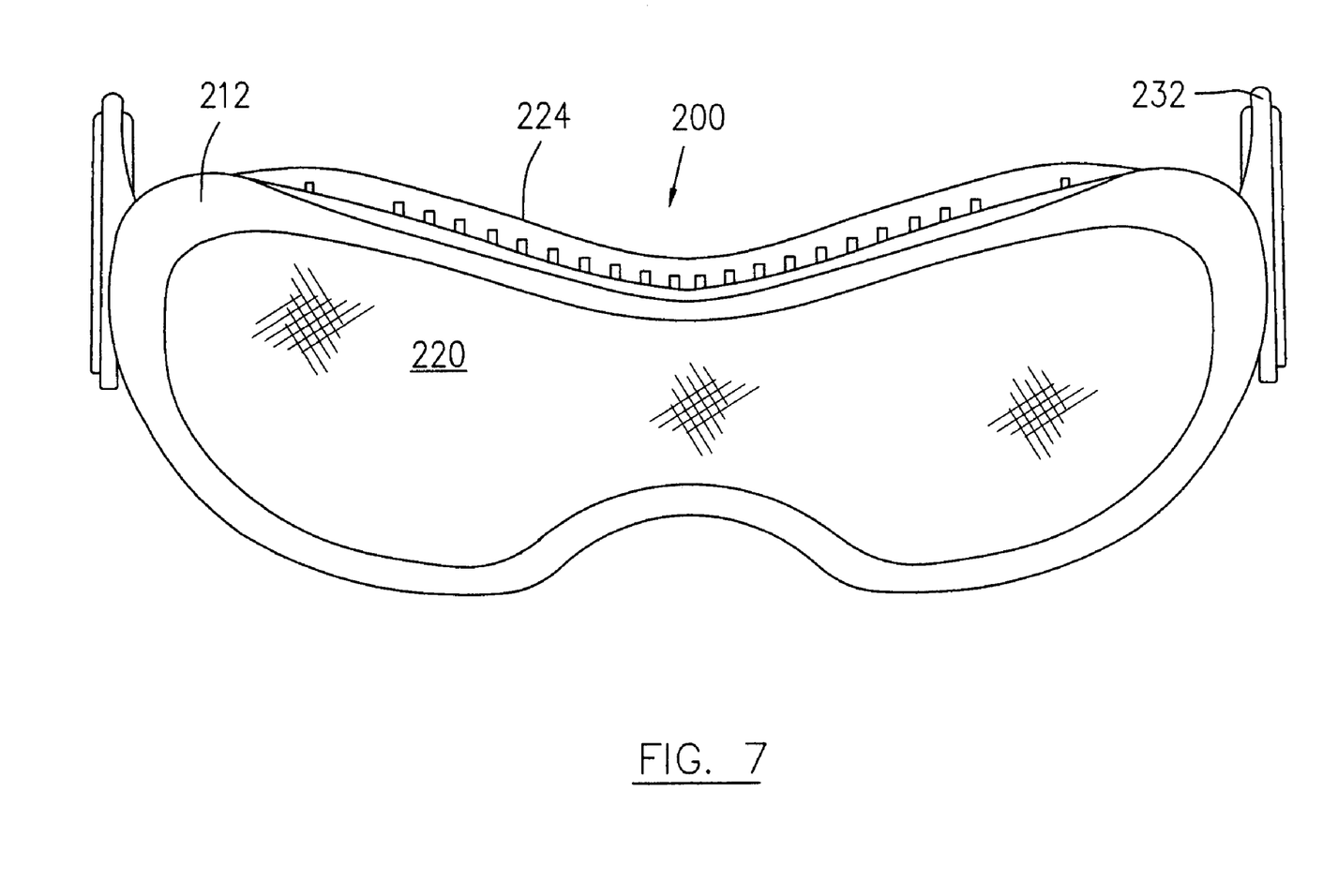
FIG. 7 is a front elevational view of a goggle in accordance with another embodiment of the present invention.

FIG. 7 illustrates a further embodiment of the eyewear of the present invention in which a single lens goggle 200 is similar to the goggles 10 of FIGS. 1-3 and will not be redundantly described. The goggle 200 includes a single lens 220 secured to a frame 212 thereof. The goggle 200 includes a shielding member 224 and flexible side mounting tabs 232 similar to the shielding member 24 and the flexible side mounting tabs 32 of goggles 10 in FIGS. 1-3. The single lens goggle 200 is illustrated as an example to show the suitable application of the present invention to goggles having either a single lens or a pair of lenses.

As an alternative, the side mounting tabs can be integrally made together with the frame from a material having a resilient property to form flexible extensions of the opposite side ends of the frame. Thus, the flexible side mounting tabs allow displacement of the attachment position of the head support (head strap) to the side mounting tabs, with respect to the frame. Preferably, the configuration of the frame provides a substantially rigid property thereto, excluding the integrated side mounting tabs.

The above-description is meant to be exemplary only and one skilled in the art will recognize that changes may be made to the embodiments described without departure from the scope of the invention disclosed. For example, the eyewear frame is preferably substantially rigid, however semi-rigid or resilient materials can also be used for eyewear frames provided that the flexibility and resiliency of the material used for the frame is less than the flexibility and resilience of the material used for the side mounting tabs, in order to maintain the desirable shape of the eyewear. The particular configuration of the side mounting tabs can vary such as one in which the head strap is secured to the side mounting tabs rather than through the elongate opening 40, 140. The shielding member of the goggles can also be of various configurations other than that described. For example, a plurality of shielding members of flexible and/or resilient materials can be placed in a spaced apart relationship around the lens or lenses at the inner surface of the frame. The shielding member can also be integrally formed with the frame during the formation of the frame if the frame is made of semi-rigid or resilient materials. Still other modifications which fall within the scope of the present invention will be apparent to those skilled in the art, in light of a review of this disclosure, and such modifications are intended to fall within the scope of the appended claims.

I claim:

1. Eyewear comprising:

at least one lens;

a frame made of a first material, having opposite side ends thereof, the frame securing the at least one lens thereto;

means contoured for surrounding and shielding the eyes of a user;

a head support for holding the eyewear on a user's head in a manner such that said means are forced to abut an area around the eyes of the user; and a pair of side mounting tabs each having opposite first and second ends thereof, secured at the first end thereof to the respective side ends of the frame, the head support being attached to the respective side mounting tabs at the second end thereof, and the side mounting tabs being made of a resilient second material to provide a flexibility of the tabs, each of the side mounting tabs including a reinforced section at the second end thereof such that the reinforced section at the second end is less flexible than an intermediate section of the side mounting tab between the reinforced section at the second end and a section at the first end which is secured to the frame.

2. The eyewear as claimed in claim 1 wherein each of the side mounting tabs comprises a top and a bottom extending between the first and second ends, and a plurality of grooves extending between the top and the bottom in order to increase the flexibility of the tabs.

3. The eyewear as claimed in claim 1 wherein the head support comprises a flexible strap.

4. The eyewear as claimed in claim 3 wherein the strap is made of an elastic material.

5. The eyewear as claimed in claim 3 wherein each of the side mounting tabs comprises an opening for attachment of the strap thereto.

6. The eyewear as claimed in claim 1 wherein each of the side mounting tabs is molded onto the side end of the frame.

7. The eyewear as claimed in claim 1 wherein each of the side mounting tabs is glued onto the side end of the frame.

8. The eyewear as claimed in claim 1 wherein each of the side mounting tabs is secured to the side end at inner side of the frame with at least one insert projecting into the frame towards an outer side of the frame.

9. The eyewear as claimed in claim 1 wherein the first material is substantially rigid with respect to the second material.

10. A pair of goggles comprising:

a pair of lenses;

a frame made of a first material and having opposite side ends thereof, the frame securing the pair of lenses thereto;

one or more shielding members attached to the frame and contoured for surrounding and shielding the eyes of a user;

a flexible and resilient strap for holding the goggles on the head of the user; and a pair of side mounting tabs integrally secured to the frame at the respective opposite side ends thereof for attachment of the strap, the side mounting tabs being made of a second material which is flexible and resilient, each of the side mounting tabs including a reinforced section at a second end thereof for attaching the strap such that the reinforced section is less flexible than an intermediate section of the side mounting tab between the reinforced section at a first end of the side mounting tab secured to the frame.

11. The goggles as claimed in claim 10 wherein the first material is less flexible and less resilient than the second material.

12. The goggles as claimed in claim 10 wherein the first material is substantially rigid with respect to the second material.

* * * * *